US009055757B2

(12) United States Patent
Tan et al.

(10) Patent No.: US 9,055,757 B2
(45) Date of Patent: Jun. 16, 2015

(54) STABILIZER COMPOSITION OF CO-ATTRITED MICROCRYSTALLINE CELLULOSE AND CARBOXYMETHYLCELLULOSE, METHOD FOR MAKING, AND USES

(71) Applicant: FMC Corporation, Philadelphia, PA (US)

(72) Inventors: Zheng Tan, Princeton, NJ (US); Maurice Gerard Lynch, Waterloo (BE); Thomas Ruszkay, Hockessin, DE (US); Michael Sestrick, Yardley, PA (US)

(73) Assignee: FMC Corporation, Philadelphia, PA (US)

( * ) Notice: Subject to any disclaimer, the term of this patent is extended or adjusted under 35 U.S.C. 154(b) by 168 days.

(21) Appl. No.: 13/573,764

(22) Filed: Oct. 4, 2012

(65) Prior Publication Data
US 2013/0090391 A1 Apr. 11, 2013

Related U.S. Application Data

(60) Provisional application No. 61/543,660, filed on Oct. 5, 2011.

(51) Int. Cl.
| A23K 1/00 | (2006.01) |
| A01N 25/00 | (2006.01) |
| A23L 1/212 | (2006.01) |
| A23L 2/52 | (2006.01) |
| A23L 1/0534 | (2006.01) |
| A61Q 11/00 | (2006.01) |
| A61K 8/73 | (2006.01) |
| A61Q 19/00 | (2006.01) |
| A61K 8/02 | (2006.01) |
| A23C 9/154 | (2006.01) |
| B01J 13/00 | (2006.01) |

(52) U.S. Cl.
CPC ............... *A23L 1/2128* (2013.01); *A23L 2/52* (2013.01); *A23L 1/0534* (2013.01); *A61Q 11/00* (2013.01); *A61K 8/731* (2013.01); *A61Q 19/00* (2013.01); *A61K 8/022* (2013.01); *A61K 2800/48* (2013.01); *A61K 2800/594* (2013.01); *A23C 9/1544* (2013.01); *B01J 13/0052* (2013.01)

(58) Field of Classification Search
CPC ............. A23L 1/0534; A61K 2800/48; A61K 2800/594; A61K 47/38; A61K 8/73; A01N 25/22
USPC ............................. 516/106; 514/781; 426/615
See application file for complete search history.

(56) References Cited

U.S. PATENT DOCUMENTS

| 2,978,446 | A | 4/1961 | Battista et al. |
| 3,023,104 | A | 2/1962 | Battista et al. |
| 3,145,146 | A | 8/1964 | Lieberman et al. |
| 3,146,168 | A | 8/1964 | Battista |
| 3,539,365 | A | 11/1970 | Durand et al. |
| 3,573,058 | A | 3/1971 | Tiemstra |
| 3,639,169 | A | 2/1972 | Broeg et al. |
| 4,017,598 | A | 4/1977 | Ohno et al. |
| 4,110,476 | A | 8/1978 | Rhodes |
| 4,263,334 | A | 4/1981 | McGinley |
| 4,264,637 | A | 4/1981 | Braverman |
| 4,426,518 | A | 1/1984 | Omiya |
| 4,693,750 | A | 9/1987 | Bauer et al. |
| 4,744,987 | A | 5/1988 | Mehra et al. |
| 4,980,193 | A | 12/1990 | Tuason, Jr. et al. |
| 5,082,684 | A | 1/1992 | Fung |
| 5,192,569 | A | 3/1993 | McGinley et al. |
| 5,272,137 | A | 12/1993 | Blase et al. |
| 5,286,510 | A | 2/1994 | Bauer et al. |
| 5,366,724 | A | 11/1994 | Pierre et al. |
| 5,366,742 | A | 11/1994 | Tuason, Jr. et al. |
| 5,409,907 | A | 4/1995 | Blase et al. |
| 5,415,804 | A | 5/1995 | Minami |
| 5,505,982 | A | 4/1996 | Krawczyk et al. |
| 5,543,511 | A | 8/1996 | Bergfeld et al. |
| 5,573,777 | A | 11/1996 | Serpelloni et al. |
| 5,605,712 | A | 2/1997 | Bertrand et al. |
| 5,607,716 | A | 3/1997 | Doherty et al. |
| 5,609,898 | A | 3/1997 | Kaji et al. |
| 5,709,896 | A | 1/1998 | Hartigan et al. |
| 5,725,886 | A | 3/1998 | Erkoboni et al. |
| 5,747,067 | A | 5/1998 | Auguello et al. |
| 5,769,934 | A | 6/1998 | Ha et al. |
| 5,789,004 | A | 8/1998 | Hogan et al. |
| 5,866,166 | A | 2/1999 | Staniforth et al. |

(Continued)

FOREIGN PATENT DOCUMENTS

| EP | 1226818 A1 | 7/2002 |
| EP | 1 681 048 A1 | 7/2006 |

(Continued)

OTHER PUBLICATIONS

Sigma product information of carboxymethylcellulose sodium salt (published Aug. 2003).*
Notification of Transmittal of the International Search Report and the Written Opinion of the International Searching Authority, or the Declaration, International Filing Date Oct. 4, 2012, International Application No. PCT/US 2012/000482.
Mitchell, S.A., et al., 'A Compaction Process to enhance dissolution of poorly water-soluble drugs using hydroxypropyl methylcellulose'. International Journal of Pharmaceutics, 250, pp. 3-11, 2003.
Kleinebudde, P., 'Roll Compaction/Dry Granulation: Pharmaceutical Applications'. European Journal of Pharmaceutics and biopharmaceutics, 58, pp. 317-326, 2004.
Deyampertrogers, Tracey L., 'Content Considerations for Low Dosage Drug B3 Formulations Processed by Roller Compaction'. Ph.D. Thesis, Purdue University, Aug. 1997.
Deyampert Rogers, Tracey L., 'Oral Preliminary Examination', Sep. 1, 1995.
Falzone, Angela Marie, 'Roller Compaction of Pharmaceutical Excipients and Excipient-drug Blends'. Ph.D. Thesis, Purdue University, Dec. 1990.

(Continued)

*Primary Examiner* — Sean Basquill
*Assistant Examiner* — Andrew S Rosenthal
(74) *Attorney, Agent, or Firm* — FMC Corporation

(57) ABSTRACT

Methods of making a high gel strength, water-dispersible, stabilizing colloidal microcrystalline cellulose composition are disclosed. This stabilizer composition is useful in many food and non-food applications.

33 Claims, No Drawings

(56) References Cited

U.S. PATENT DOCUMENTS

| | | | |
|---|---|---|---|
| 6,010,734 A | 1/2000 | Whelan et al. | |
| 6,025,007 A | 2/2000 | Krawczyk | |
| 6,037,380 A * | 3/2000 | Venables et al. | 514/781 |
| 6,079,630 A | 6/2000 | Schroeder | |
| 6,106,865 A | 8/2000 | Staniforth et al. | |
| 6,117,474 A | 9/2000 | Kamada et al. | |
| 6,228,213 B1 | 5/2001 | Hanna et al. | |
| 6,235,947 B1 | 5/2001 | Yoshinari et al. | |
| 6,264,981 B1 | 7/2001 | Zhang et al. | |
| 6,270,830 B1 | 8/2001 | Kamada et al. | |
| 6,368,649 B1 | 4/2002 | van Bommel | |
| 6,372,782 B1 | 4/2002 | Patel et al. | |
| 6,391,368 B1 | 5/2002 | Tuason et al. | |
| 6,432,448 B1 | 8/2002 | Augello et al. | |
| 6,440,474 B1 | 8/2002 | Buliga et al. | |
| 6,475,539 B1 | 11/2002 | Dewille et al. | |
| 6,500,462 B1 | 12/2002 | Augello et al. | |
| 6,503,918 B2 | 1/2003 | Yoshinari et al. | |
| 6,517,871 B1 | 2/2003 | Venkatesh et al. | |
| 6,548,093 B1 | 4/2003 | Collinge et al. | |
| 6,689,405 B1 | 2/2004 | Tuason, Jr. et al. | |
| 6,709,713 B2 | 3/2004 | Augello et al. | |
| 6,723,342 B1 | 4/2004 | Augello et al. | |
| 6,726,949 B2 | 4/2004 | Adolphi et al. | |
| 6,752,939 B2 | 6/2004 | Gereg | |
| 6,753,017 B2 | 6/2004 | Berkulin et al. | |
| 6,936,277 B2 | 8/2005 | Staniforth et al. | |
| 6,936,628 B2 | 8/2005 | Lee | |
| 7,462,232 B2 | 12/2008 | Tuason et al. | |
| 7,625,622 B2 | 12/2009 | Teckoe et al. | |
| 7,785,089 B2 | 8/2010 | Teckoe et al. | |
| 7,879,382 B2 | 2/2011 | Tuason et al. | |
| 2003/0017204 A1 | 1/2003 | Augello et al. | |
| 2003/0129238 A1 | 7/2003 | Augello et al. | |
| 2004/0071821 A1 | 4/2004 | Ashourian et al. | |
| 2004/0121006 A1 | 6/2004 | Narita et al. | |
| 2004/0137043 A1 | 7/2004 | Augello et al. | |
| 2004/0185161 A1 | 9/2004 | Ashourian et al. | |
| 2005/0147710 A1 | 7/2005 | Teckoe et al. | |
| 2005/0220824 A1 | 10/2005 | Kessel et al. | |
| 2005/0233046 A1 | 10/2005 | Krawczyk et al. | |
| 2005/0233053 A1 | 10/2005 | Shen et al. | |
| 2005/0266116 A1 | 12/2005 | Teckoe et al. | |
| 2006/0008575 A1 | 1/2006 | Armbrecht et al. | |
| 2006/0096500 A1 * | 5/2006 | Tuason et al. | 106/162.1 |
| 2006/0127451 A1 | 6/2006 | Augello et al. | |
| 2007/0264407 A1 | 11/2007 | Cerdena | |
| 2008/0131505 A1 | 6/2008 | Li et al. | |
| 2008/0131543 A1 | 6/2008 | Teckoe et al. | |
| 2008/0213360 A1 | 9/2008 | Thoorens et al. | |
| 2009/0110799 A1 | 4/2009 | Funami et al. | |
| 2009/0130287 A1 | 5/2009 | Tuason et al. | |
| 2011/0143009 A1 | 6/2011 | Tuason et al. | |
| 2011/0151097 A1 | 6/2011 | Tuason et al. | |
| 2013/0064953 A1 * | 3/2013 | Bache et al. | 426/573 |

FOREIGN PATENT DOCUMENTS

| | | |
|---|---|---|
| GB | 1010477 | 11/1965 |
| GB | 1 567 049 | 5/1980 |
| GB | 1567049 A | 5/1980 |
| GB | 2395413 A | 5/2004 |
| JP | 08-151481 A | 6/1996 |
| JP | 9266779 | 10/1997 |
| JP | 10-056960 | 3/1998 |
| JP | 10-237220 A | 9/1998 |
| JP | 11-046723 A | 2/1999 |
| JP | 11-299435 A | 11/1999 |
| JP | 2000-184853 | 7/2000 |
| JP | 2001-190220 A | 7/2001 |
| JP | 2002-125587 A | 5/2002 |
| JP | 2002345401 A2 | 12/2002 |
| JP | 2005-245217 | 9/2005 |
| SU | 467105 | 4/1975 |
| WO | WO 81-02521 A1 | 9/1981 |
| WO | WO 94/24888 A1 | 11/1994 |
| WO | WO 9502966 | 2/1995 |
| WO | WO 98/56826 A1 | 12/1998 |
| WO | WO 00/04862 A2 | 2/2000 |
| WO | WO 01/19348 A1 | 3/2001 |
| WO | WO 0132150 | 5/2001 |
| WO | WO 0132152 | 5/2001 |
| WO | WO 02/49451 A2 | 6/2002 |
| WO | WO 03/003843 A1 | 1/2003 |
| WO | WO 03/090558 A1 | 11/2003 |
| WO | WO 03/096976 A2 | 11/2003 |
| WO | WO 2005/030177 A2 | 4/2005 |
| WO | WO 2005/096832 A2 | 10/2005 |
| WO | WO 2006/131936 A1 | 12/2006 |
| WO | WO 2010/136157 | 12/2010 |
| WO | WO 2010136157 A1 | 12/2010 |

OTHER PUBLICATIONS

Skinner, G.W., 'The Evaluation of Fine-particle Hydroxyprpycellulose as a Roller Compaction binder in Pharmaceutical Applications'. Drug Development & Indust. Pharm, 25(10), pp. 1121-1128, 1999.

The Fitzpatrick Company Europe N.V., 'Introduction to Roll Compaction and the Fitzpatrick Chilsonator'. Mar. 1997.

Sheskey, P., et al. 'Roll Compaction Granulation of a Controlled-Release Matrix Tablet Formulation Containing HPMC'. Pharmaceutical Technology, Oct. 1999.

Zhang, Y., et al., 'Physical Properties and Compact Analysis of Commonly Used Direct Compression Binders'. AAPS Pharm. Sci. Tech. 4 (4) Article 62, Dec. 15, 2003.

Hsiu-O, H. et al., 'Characteristics of Codried Products of Microcrystalline Cellulose with Saccharides and Low-substituted Hydroxypropylcellulose'. Powder Technology, 127 2002, pp. 45-53.

Gohel, M.C., 'A Review of Co-processed Directly Compressible Excipients'. Journal of Pharma, Pharma. Sci. 8(1), pp. 76-93, 2005.

Schroder, R. et al., 'Influence of Magnesium Stearate on the Compaction Behavior and Tablet characteristics of Co-Spray Dried Compounds vs Physical Blends'. Poster Presented at American Association of Pharmaceutical Science (Denver) Oct. 2001.

Jacob, S. et al. 'Novel Co-processed Excipients of Mannitol and Microcrystalline Cellulose for Preparing Fast Dissolving Tablets of Glipzide'. Indian Journal of Pharmaceutical Sciences, vol. 69 (5) Sep.-Oct. 2007, pp. 633-639.

Rowe, Sheskey & Weller, "Handbook of Pharmacuetical Excipients, Fourth Edition", 2003, Pharmaceutical Press, London. XP002281910, p. 110, column 2.

Sigma product info of carboxymethylcellulose, sodium salt (published Aug. 2003).

Bowman, B.J. Ofner, C.M.; Schott, H. "Colloidial Dispersions" Chapter 21 of Remington: The Science and Practice of Pharmacy, 21$^{st}$ Edition, 2005, Lippincott Williams and Wilkins, Philadelphia, PA.

* cited by examiner

STABILIZER COMPOSITION OF CO-ATTRITED MICROCRYSTALLINE CELLULOSE AND CARBOXYMETHYLCELLULOSE, METHOD FOR MAKING, AND USES

FIELD OF THE INVENTION

The invention relates to methods of making microcrystalline cellulose:carboxymethyl cellulose compositions for use as a stabilizer and dispersant in aqueous media of certain dry, powered materials, particularly in food applications.

BACKGROUND OF THE INVENTION

Microcrystalline cellulose, also known as MCC or cellulose gel, is commonly used in the food industry to enhance the properties or attributes of a final food product. For example, it has been used as a binder and stabilizer in food applications, including in beverages, and as stabilizers. It has also been used as a binder and disintegrant in pharmaceutical tablets, as a suspending agent in liquid pharmaceutical formulations, and as binders, disintegrants, and processing aids in industrial applications, in household products such as detergent and/or bleach tablets, in agricultural formulations, and in personal care products such as dentifrices and cosmetics.

Microcrystalline cellulose is produced by treating a source of cellulose, preferably alpha cellulose in the form of pulp from fibrous plant materials, with a mineral acid, preferably hydrochloric acid (acid hydrolysis). The acid selectively attacks the less ordered regions of the cellulose polymer chain thereby exposing and freeing the crystalline sites which form crystallite aggregates which constitute the microcrystalline cellulose. These are then separated from the reaction mixture, and washed to remove degraded by-products. The resulting wet mass, generally containing 40 to 60 percent moisture, is referred to in the art by several names, including 'hydrolyzed cellulose', 'hydrolyzed cellulose wetcake', 'level-off DP cellulose', 'microcrystalline cellulose wetcake', or simply 'wetcake'.

The classic process for MCC production is acid hydrolysis of purified cellulose, pioneered by O. A. Battista (U.S. Pat. Nos. 2,978,446; 3,023,104; and 3,146,168). In efforts to reduce the cost while maintaining or improving the quality of MCC, various alternative processes have been proposed. Among these are steam explosion (U.S. Pat. No. 5,769,934; Ha et al.), reactive extrusion (U.S. Pat. No. 6,228,213; Hanna et al.), one-step hydrolysis and bleaching (World Patent Publication WO 01/0244; Schaible et al.), and partial hydrolysis of a semi-crystalline cellulose and water reaction liquor in a reactor pressurized with oxygen and/or carbon dioxide gas and operating at 100 to 200° C. (U.S. Pat. No. 5,543,511; Bergfeld et al.).

Microcrystalline cellulose and/or hydrolyzed cellulose wetcake has been modified for a variety of uses. In food products it is used as a gelling agent, a thickener a fat substitute and/or non-caloric filler, and as a suspension stabilizer and/or texturizer. It has also been used as an emulsion stabilizer and suspending agent in pharmaceutical and cosmetic lotions and creams. Modification for such uses is carried out by subjecting micro-crystalline cellulose or wetcake to intense attrition (high shear) forces as a result of which the crystallites are substantially subdivided to produce finely divided particles. However, as particle size is diminished, the individual particles tend to agglomerate or hornify upon drying. A protective colloid (such as sodium carboxy-methylcellulose (CMC)) may be added during attrition or following attrition but before drying. The protective colloid wholly or partially neutralizes the hydrogen or other bonding forces between the smaller sized particles. Colloidal microcrystalline cellulose, such as the carboxymethyl cellulose-coated microcrystalline cellulose described in U.S. Pat. No. 3,539,365 (Durand et al.). This additive also facilitates re-dispersion of the material following drying. The resulting material is frequently referred to as attrited microcrystalline cellulose or colloidal microcrystalline cellulose.

On being dispersed in water, colloidal microcrystalline cellulose forms white, opaque, thixotropic gels with microcrystalline cellulose particles less than 1 micron in size. FMC Corporation (Philadelphia, Pa., USA) manufactures and sells various grades of this product which comprise co-processed microcrystalline cellulose and sodium carboxymethylcellulose under the designations of, among others, AVICEL® and GELSTAR®.

There remains a need, however, for a method of making a colloidal microcrystalline cellulose:carboxymethyl cellulose composition with enhanced stabilization, improved gel strength G', and other desirable rheological properties useful in a variety of applications, and particularly in food products.

SUMMARY OF THE INVENTION

The present invention provides a method of making a colloidal microcrystalline cellulose. The resulting inventive product exhibits a high gel strength G' of greater than 20 Pa, preferably greater than 40 Pa, and is useful as a stabilizer and dispersant in edible food products.

The method of the present invention comprises extruding with sufficient attriting intensity an admixture comprising i) a microcrystalline cellulose wetcake having a solids content of at least about 42%; and ii) a carboxymethylcellulose having a degree of substitution of 0.45 to 0.85, wherein the weight ratio of microcrystalline cellulose to carboxymethylcellulose is from 95:5 to 70:30 of the combined weight of the solids. One embodiment uses a particular weight ratio of microcrystalline cellulose wetcake to carboxymethylcellulose of 85:15. The admixture is extruded with high shear/high compression treatment and the product is dried.

If the carboxymethylcellulose used has a low viscosity ranging from 10 to 200 cps, preferably from 10 to 100 cps, and more preferably from 30 to 60 cps, the product thus made and upon dispersion in water at 2.6% solids exhibits a) an initial viscosity of at least 750 cps, more preferably 1000 to 3000 cps, b) a set up viscosity after 24 hours of at least 2900 cps, more preferably 3000 to 7500 cps, more preferably, 3000 to 7200 cps, and c) a gel strength G' of at least 20 Pa, preferably of at least 25 Pa, and more preferably of 30 Pa to 100 Pa.

If the carboxymethylcellulose used has a medium viscosity ranging from 200 to 4000 cps, preferably from 200 to 3000 cps, and more preferably from 300 to 900 cps, the product thus made and upon dispersion in water at 2.6% solids, exhibits a) an initial viscosity of at least 1000 cps, at least 2000 cps, preferably at least 2500, and more preferably 2500-4500 cps, b) a set up viscosity after 24 hours of at least 3500 cps, preferably 3500-7500 cps, and c) a gel strength G' of at least 40 Pa, and preferably of 40 to 100 Pa.

In one embodiment, the solids content of the microcrystalline cellulose wetcake is at least about 42% to 60%, preferably from 42.5% to 55%, and, more preferably, at least about 42.5% to 50%. The microcrystalline cellulose wetcake material optionally may be made more amenable to co-attrition with extended cooking time or chemical or mechanical treatments before being co-processed.

In one embodiment, the carboxymethylcellulose has a degree of substitution of 0.45 to 0.85, more preferably of 0.45 to 0.80, and most preferably of about 0.7. In another embodiment, the carboxymethylcellulose is an alkali carboxymethyl cellulose, most preferably sodium carboxymethyl cellulose.

Further embodiments encompass a food product comprising the stabilizer composition produced by the disclosed methods. A further embodiment encompasses a suspension comprising the stabilizer composition adapted for use in pharmaceutical products, nutraceutical products, healthcare products, cosmetic products, personal care products, consumer products, agricultural products, or chemical formulations.

Other features and advantages of the foregoing embodiments will be apparent from the following detailed description and from the claims. The disclosed embodiments are exemplary and explanatory only and not to be considered to be restrictive of the invention.

DETAILED DESCRIPTION OF THE PREFERRED EMBODIMENTS

The present disclosure encompasses a water-dispersible colloidal microcrystalline cellulose made of at least 42% solids wetcake co-attrited with a carboxymethylcellulose of a low degree of substitution (DS). The product, when a low viscosity carboxymethylcellulose is used, provides high gel strength G' of greater than 20 Pa (when measured as a 2.6% dispersion in water) and is useful as a stabilizer in edible food products. The product, when a medium viscosity carboxymethylcellulose is used, provides high gel strength G' of greater than 40 Pa (when measured as a 2.6% dispersion in water) and is useful as a stabilizer in edible food products.

"Colloid" and "colloidal" are used interchangeably in the specification to define particles that may be suspended in a mixture. As known to those of ordinary skill in the art, colloidal particles are of a certain average particle size, for example, on the order of about 0.1 to 10 microns. The colloidal particles described herein may be of any suitable particles size, provided that they are able to form colloidal suspensions.

"Gel" refers to a soft, solid, or solid-like material which consists of at least two components, one of which is a liquid present in abundance (Almdal, K., Dyre, J., Hvidt, S., Kramer, O.; Towards a phenomological definition of the term 'gel'. *Polymer and Gel Networks* 1993, 1, 5-17).

"Gel strength G'" refers to the reversibly stored energy of the system (the elastic modulus G') and relative to the compositions herein is a function of the cellulose concentration. The measurement is made with a TA-Instruments rheometer (ARES-RFS3) with oscillatory strain sweep at 1 Hz and at 20° C., with gap size at 1.8 mm. Testing is performed 24 hours set up of a 2.6% solids dispersion of the composition in deionized water.

The Brookfield viscosity test is used to obtain an initial viscosity on the activated compositions (2.6% solids dispersion of the material in deionized water) and repeated to obtain viscosity after 24 hours. A RVT viscometer, with an appropriate spindle, is used at 20 rpm, at 20° to 23° C.

Methods for forming the compositions are provided. The methods include mixing a water-soluble carboxymethylcellulose having a low degree of substitution with microcrystalline cellulose wetcake of at least 42% solids, wherein the weight ratio of the microcrystalline cellulose to the carboxymethylcellulose is about 95:5 to about 70:30. A particular weight ratio of the microcrystalline cellulose to the carboxymethylcellulose is about 90:10 to about 70:30; a more particular weight ratio of the microcrystalline cellulose to the carboxymethylcellulose is about 90:10 to about 80:20. In one embodiment, the particular weight ratio is 85:15.

The moist mixture is extruded with sufficient intensity to effect intimate mixing to achieve sufficient co-attrition and microcrystalline cellulose:carboxymethylcellulose interaction among the components. As used in this specification, the terms "attrited" and "attrition" are used interchangeably to mean a process that effectively reduces the size of at least some if not all of the particles to a colloidal size. The processing is a mechanical processing that introduces shearing force either to an MCC wetcake before blending with CMC or to an admixture of MCC wetcake and CMC. "Co-attrition" is used to refer to applications of high shear forces to an admixture of the MCC and CMC component. Suitable attrition conditions may be obtained, for example, by co-extruding, milling, or kneading.

The extrudate can be dried or be dispersed in water to form a slurry. The slurry can be homogenized and dried, preferably spray dried. Drying processes other than spray drying include, for example, fluidized bed drying, drum drying, bulk drying, and flash drying. Dry particles formed from the spray drying can be reconstituted in a desired aqueous medium or solution to form the compositions, edible food products, and industrial applications described herein.

The MCC:CMC extrusions disclosed herein are done at high intensity with high shear and high compression, so that the resulting colloidal MCC product is sufficiently attrited. As used herein, "shear force" refers to an action resulting from applied force that causes or tends to causes two contiguous parts of a mixture to slide relative to each other in a direction generally parallel to their plane of contact. The amount of force applied must be sufficient to create associations between the microcrystalline cellulose particles and the carboxymethylcellulose. If the force applied is insufficient, the components remain too "slippery" to transfer the shear force applied to the material or admixture to accomplish intimate associations. In that case, the shear force is primarily dissipated as mechanical energy by sliding action. Any means to increase the extrusion intensity may be used, including, but not limited to, extruder designs, duration/passes of extrusions, extrusion with attriting aids including all mentioned by FMC patent U.S. Pat. No. 6,037,380 (Venables et al.), high shear/high solids levels, and anti-slip agents.

A preferred way of effecting high extrusion intensity controls the solids level of the microcrystalline cellulose wetcake to be extruded. A wetcake solids level below about 41% yields a colloidal MCC with a given gel viscosity and gel strength G'. However, if the wetcake solids content is higher than about 42%, the final colloidal MCC product shows a significant increase in gel strength G'. The comprehensive range of the effective wetcake solids level is between about 42% to 60%, preferably 42.5% to 60%, more preferably 42.5% to 55%, and most preferably 43% to 50%.

Strategies to increase the wetcake solids content include, but are not limited to, better dewatering during washing/filtering with more vacuum/felting/pressing/filter surface areas, in-line evaporation of water from the wetcake before CMC addition by steam heating, hot air flows, Infrared irradiation, and RF/microwave heating. Another strategy is to add dry (or higher solids) MCC (or colloidal MCC such as Avicel RC591 or Avicel CL611 powders) into the wetcake, thereby increasing the total MCC solids content of the composition.

Improved extrusion/attrition intensity may be done with extended extrusion residence time (or more passes), and may also be achieved by cooling the extrusion temperature. The use of any common coolants is included in the invention's embodiments, and includes, but is not limited to, water cooling, and ammonia cooling.

In another embodiment, sufficient extrusion/attrition may be achieved in two or more separate steps. For instance, the MCC wetcake may be extruded/attrited first and then followed by CMC addition and extrusion/attrition. In addition to various types of extruders as practiced in current MCC manufacturing, equipment for attriting MCC wetcake or MCC:CMC include compression rolls/belts, calendaring rolls, mechanical refiner discs, ultrasonic refiners, high pressure homogenizers (including Micro-fluidic devices), high compression planetary mixers, and shockwave/cavitation devices.

Microcrystalline Cellulose Wetcake:

MCC from any source may be employed in the methods. Suitable feedstocks from which MCC may be obtained include, for example, wood pulp [such as bleached sulfite and sulfate pulps], corn husks, bagasse, straw, cotton, cotton linters, flax, hemp, ramie, seaweed, cellulose, and fermented cellulose. Additional feedstocks include bleached softwood kraft pulps, bleached hardwood kraft pulps, bleached Eucalyptus kraft pulps, paper pulps, fluff pulps, dissolving pulps, and bleached non-wood cellulosic pulps. In one embodiment, the MCC used is one approved for human consumption by the United States Food and Drug Administration.

If desired, the MCC may be made from a low cost pulp or mixtures of low cost pulp and specialty pulp. If a mixture is desired, then, for example, 30-80% of the total MCC can be from made from low cost pulp, and the colloidal content of the resulting MCC product can be at least 60%. Examples of low cost pulp include any paper grade pulp and fluff pulp, such as Southern Bleached Softwood Kraft Pulp, Northern Bleached Softwood Pulp, Bleached Eucalyptus Kraft Pulp, Bleached Hardwood Kraft Pulp, Bleached Sulfite Pulps, Bleached Soda Pulps, and bleached nonwood pulps. Specific low cost pulps include CPH pulp from Weyerhaeuser and Viscose grade dissolving pulps.

Chemical or mechanical treatments make MCC more amenable to extrusion/attrition intensity. For instance, during MCC acid hydrolysis cooking (or after MCC acid cooking), the MCC slurry can be treated with peroxide, peracetic acid, performic acid, persulfate, or oxone at acidic pH. The acid hydrolysis process to make MCC may also be enhanced with other additives (such as iron salts, i.e., ferric chloride). Another approach is to extend the cooking time of MCC acid hydrolysis as shown in Example 5. The effect of extended cooking time may also be achieved by varying other conditions of the acid hydrolysis, including a higher acid concentration and/or increased cooking temperature.

The disclosed techniques of boosting MCC wetcake solids content and mechanically or chemically varying the treatment of the MCC may be combined to increase the gel strength G' of the final product more than by use of any technique alone.

Carboxymethylcellulose:

The carboxymethylcellulose comprises an alkali metal carboxymethylcellulose, for instance, sodium, potassium, or ammonium CMC. Most preferably, the carboxymethy cellulose is sodium CMC.

The CMC is characterized by, inter alia, the degree of substitution (DS) that is present. The degree of substitution represents the average number of hydroxyl groups substituted per anhydroglucose unit. For example, in CMC, each anhydroglucose unit contains three hydroxyl groups, which gives CMC a maximum theoretical DS of 3.0.

The CMC is also characterized by, inter alia, viscosity, as measured in a 2% aqueous solution, at 25° C. (Brookfield). "Low viscosity" CMC has a range of 10 to 200 cps (60 rpm). A particular "low viscosity" CMC has a range of 10-100 cps, and a more particular "low viscosity" CMC has a range of 30-60 cps. "Medium viscosity" CMC has a range of 200 to 4000 cps (30 rpm). A particular "medium viscosity" CMC has a range of 200-3000 cps, and a more particular "medium viscosity" CMC has a range of 300-900 cps. Two commercially available carboxymethylcelluloses are AQUALON®7LF (low viscosity) and AQUALON®7MF (medium viscosity), both with a DS of 0.7, which is an average of 7 carboxymethyl groups per 10 anhydroglucose units (Ashland, Inc., Wilmington, Del., USA).

The carboxymethylcelluloses contemplated for use in the present methods have a degree of substitution of about 0.45 to about 0.85. In some embodiments, the carboxymethylcellulose has a degree of substitution of 0.45 to 0.80. In still other embodiments, the carboxymethylcellulose has a degree of substitution of about 0.7.

Colloidal MCC:CMC Compositions:

The disclosed colloidal MCC:CMC compositions based on low degrees of substitution CMC and at least 42% solids content of MCC wetcake have significantly improved gel strength G', as well as improved rheological indices such as viscosity and colloidal content. In such cases when only low viscosity/low DS CMC is used in the colloidal MCC:CMC compositions, the gel strength G' (water dispersion at 2.6% solids) is at least 20 Pa, preferably at least 25 Pa, and more preferably at least 30 Pa. In other embodiments, the gel strength G' may be between 30-100 Pa. In the case of colloidal MCC:CMC compositions based on medium viscosity/low DS CMC, the gel strength G' is at least 35 Pa, and more particularly it is at least 40 Pa.

Comparative Material 1:

AVICEL®CL611 is a commercially available colloidal MCC using a low viscosity CMC with a DS ranging from 0.45 to 0.8. When produced using bulk drying instead of spray drying, the material is identified as AVICEL®CL612. It is manufactured by FMC Corporation, Philadelphia, Pa. When dispersed in deionized water, at 2.6% solids, it exhibited at room temperature an initial Brookfield viscosity of 50-151 cps and a set-up viscosity after 24 hrs of 2500 cps. When the 2.6% solids dispersion was measured by a Texas Instruments Rheometer after 24 hrs set-up, it exhibited a gel strength G' of 9 Pa. A colloidal content of 77% was obtained, which was determined by centrifugation of the water dispersion at 8250 rpm for 15 minutes followed by gravimetric analysis of the dried supernatant portion.

Comparative Material 2:

This is a colloidal MCC based on a CMC with a DS ranging from 0.9-1.5. It is manufactured by FMC Corporation, Philadelphia, Pa. When dispersed in deionized water, at 2.6% solids, it exhibited at room temperature an initial Brookfield viscosity of 1650 cps, and a set-up viscosity after 24 hrs of 3250 cps. When the 2.6% solids dispersion was measured by a Texas Instruments Rheometer after 24 hrs set-up, it exhibited a gel strength G' of 15 Pa. A colloidal content of 80% was obtained, which was determined by centrifugation of the water dispersion at 8250 rpm for 15 minutes followed by gravimetric analysis of the dried supernatant portion.

Comparative Material 3:

AVICEL®RC-591 is a dispersible, colloidal MCC comprising a medium viscosity/low DS CMC. It is manufactured by FMC Corporation, Philadelphia, Pa. It is used in food and pharmaceutical suspensions to regulate and modify viscosity and for its thixotropic characteristics. It is heat and freezethaw stable, has long shelf-life stability, is stable at pH range 4-11, and is odorless/tasteless.

When dispersed in deionized water, at 1.2% solids, it exhibited at room temperature an initial Brookfield viscosity of 40-175 cps, and a set-up viscosity after 24 hrs of 900 to 1600 cps. When the 1.2% solids dispersion was measured by a Texas Instruments Rheometer after 24 hrs set-up, it exhibited a gel strength G' of 23 Pa. When dispersed at 2.6% solids in water, the material exhibited a gel strength G' of 30 Pa.

If desired, the stabilizer composition of the present invention can be a mixture of the microcrystalline cellulose and both low viscosity and medium viscosity carboxymethylcelluloses having a degree of substitution of 0.45-0.85, wherein the weight ratio of the microcrystalline cellulose and the combined carboxymethylcelluloses is from about 95:5 to about 70:30. Upon dispersal in water at 2.6% solids, such a mixture may have an initial viscosity of at least 2000 cps, a set-up viscosity of at least 3500 cps, and a set-up gel strength G' of at least 40 Pa.

Applications:

Edible food products are disclosed that are formed from the present compositions. These food products may include emulsions, beverages, sauces, soups, syrups, dressings, films, dairy and non-dairy milks and products, frozen desserts, cultured foods, bakery fillings, and bakery cream. The edible food products can additionally comprise diverse edible material and additives, including proteins, fruit or vegetable juices, fruit or vegetable pulps, fruit-flavored substances, or any combination thereof.

These food products can also include other edible ingredients such as, for example, mineral salts, protein sources, acidulants, sweeteners, buffering agents, pH modifiers, stabilizing salts, or a combination thereof. Those skilled in the art will recognize that any number of other edible components may also be added, for example, additional flavorings, colorings, preservatives, pH buffers, nutritional supplements, process aids, and the like. The additional edible ingredients can be soluble or insoluble, and, if insoluble, can be suspended in the food product. Routine adjustment of the composition is fully within the capabilities of one having skill in the art and is within the scope and intent of the present invention. These edible food products can be dry mix products (instant sauces, gravies, soups, instant cocoa drinks, etc.), low pH dairy systems (sour cream/yogurt, yogurt drinks, stabilized frozen yogurt, etc.), baked goods, and as a bulking agent in non-aqueous food systems and in low moisture food systems.

Suitable juices incorporating the stabilizer composition include fruit juices (including but not limited to lemon juice, lime juice, and orange juice, including variations such as lemonade, limeade, or orangeade, white and red grape juices, grapefruit juice, apple juice, pear juice, cranberry juice, blueberry juice, raspberry juice, cherry juice, pineapple juice, pomegranate juice, mango juice, apricot juice or nectar, strawberry juice, and kiwi juice) and vegetable juices (including but not limited to tomato juice, carrot juice, celery juice, beet juice, parsley juice, spinach juice, and lettuce juice). The juices may be in any form, including liquid, solid, or semi-solid forms such as gels or other concentrates, ices or sorbets, or powders, and may also contain suspended solids. In another embodiment, fruit-flavored or other sweetened substances, including naturally flavored, artificially flavored, or those with other natural flavors ("WONF"), may be used instead of fruit juice. Such fruit flavored substances may also be in the form of liquids, solids, or semi-solids, such as powders, gels or other concentrates, ices, or sorbets, and may also contain suspended solids.

Proteins suitable for the edible food products incorporating the stabilizer compositions include food proteins and amino acids, which can be beneficial to mammals, birds, reptiles, and fish. Food proteins include animal or plant proteins and fractions or derivatives thereof. Animal derived proteins include milk and milk derived products, such as heavy cream, light cream, whole milk, low fat milk, skim milk, fortified milk including protein fortified milk, processed milk and milk products including superheated and/or condensed, sweetened or unsweetened skin milk or whole milk, dried milk powders including whole milk powder and nonfat dry milk (NFDM), casein and caseinates, whey and whey derived products such as whey concentrate, delactosed whey, demineralized whey, whey protein isolate. Egg and egg-derived proteins may also be used. Plant derived proteins include nut and nut derived proteins, sorghum, legume and legume derived proteins such as soy and soy derived products such as untreated fresh soy, fluid soy, soy concentrate, soy isolate, soy flour, and rice proteins, and all forms and fractions thereof. Food proteins may be used in any available form, including liquid, condensed, or powdered. When using a powdered protein source, however, it may be desirable to prehydrate the protein source prior to blending with stabilizer compositions and juice for added stability of the resulting beverage. When protein is added in conjunction with a fruit or vegetable juice, the amount used will depend upon the desired end result. Typical amounts of protein range from about 1 to about 20 grams per 8 oz. serving of the resulting stable edible food products, such as beverages, but may be higher depending upon the application.

Other products and applications for which the present compositions may be used include non-food, industrial applications. In some embodiments, the present compositions are adapted for use as a pharmaceutical product, veterinary product, nutraceutical product, cosmetic product, personal care product, consumer product, agricultural product, or in chemical formulations. Some examples include excipients for chewable tablets, providing taste masking for drug actives (such as APAP, aspirin, ibuprofen, etc.); suspending agents; controlled release agents in pharmaceutical applications; delivery systems for flavoring agents and nutraceutical ingredients; direct compression sustained release agents, which can be used as pharmaceutical dosage forms such as tablets, films, and suspensions; thickeners, which can be used in foams, creams, and lotions for personal care applications; suspending agents, which can be used with pigments and fillers in ceramics, colorants, cosmetics, and oral care; materials such as ceramics; delivery systems for pesticides including insecticides; and other agricultural products.

In certain embodiments, the compositions are formulated as dry blends. The dry blends are suitable intermediates that can be dosed and dispersed with other ingredients including surfactants, fillers, or active substances. Sufficient water and agitation with heat are added as appropriate to activate the stabilizer in a desired food product, pharmaceutical product, nutraceutical product, personal care product, cosmetic product, consumer product, agricultural product, or chemical formulation.

Suitable surfactants include, but are not limited to, ionic or nonionic with an HLB of 1 to 40. Active substances may be added to the compositions and include, but are not limited to, at least one of a nutraceutical agent, a vitamin, a mineral, a coloring agent, a sweetener, a flavorant, a fragrance, a salivary stimulant agent, a food, an oral care agent, a breath freshening agent, a pharmaceutical active, agricultural active, therapeutic agent, cosmetic agent, chemical, buffer, or pH modifier.

Active substances can be encapsulated or otherwise processed or treated to modify their release properties.

In some embodiments, the disclosed edible food products have enhanced storage stability and, therefore, greater commercial appeal. Stable compositions are those that exhibit acceptable levels of storage stability. Storage stability is intended to mean at least one or more of the following product characteristics over the desired shelf life of the product: in liquid systems—suspension with minimal or no sedimentation, minimal or no serum separation, minimal or no creaming, minimal or no mottling, absence of rippling, absence of localized gels or gelation; in solid, semi-solid, gel, foam or film systems—minimal or no serum separation, deaeration or coalescence; and additionally for frozen systems—reduction or avoidance of the growth in size or number of ice crystals. As used in the foregoing description, minimal sedimentation means that any sediment that exists is present as loose sediment, which may be easily shaken back into the system. As used in the foregoing description, minimal serum separation means that less than 5 mm of serum is present when the liquid system is viewed in a 250 mL flask. In some embodiments, the edible food products can have enhanced storage ability without the need for adjunct stabilizers (outside of carboxymethylcelluloses used in the compositions). For example, some sauces that lack an adjunct stabilizer, such as xanthan gum, are shown to maintain relative viscosity for extended periods of time, which in some instances is at least six months.

The final beverage compositions may be processed by heat treatment in any number of ways. These methods may include, but are not limited to, pasteurization, ultra pasteurization, high temperature short time pasteurization ("HTST"), and ultra high temperature pasteurization ("UHT"). These beverage compositions may also be retort processed, either by rotary retort or static retort processing. Some compositions, such as juice-added or natural or artificially flavored soft drinks may also be cold processed. Many of these processes may also incorporate homogenization or other high shear/high compression methods. There may also be co-dried compositions, which can be prepared in dry-mix form, and then conveniently reconstituted for consumption as needed. The resulting beverage compositions may be refrigerated and stored for a commercially acceptable period of time. In the alternative, the resulting beverages may be stored at room temperature, provided they are filled under aseptic conditions.

In order to describe the invention in more detail, the following are non-limiting examples of the invention. The examples also illustrate how, in using the compositions of the inventions in finished products, one must take into consideration the many different and diverse formulation factors which determine the nature and quality of the particular product that is to be prepared.

EXAMPLES

Example 1

Using 43% Solids Wetcake to Make Colloidal MCC:CMC

MCC wetcake was obtained by acid hydrolysis cooking from the FMC facility (Newark, Del., USA). It was dewatered to a solids level of 43%. In a Hobart mixer, the MCC wetcake was admixed with Aqualon®7LF CMC (Ashland, Inc., Wilmington, Del., USA) in a ratio of 85:15 parts by weight for several minutes. The admixture was passed through a co-rotating twin-screw extruder several times with sufficient work profile. The MCC:CMC extrudate was then dispersed in deionized water. The resulting slurry was passed through a Manton Gaulin homogenizer at 2500 to 3000 psi and spray dried on a 3 foot Bowen spray dryer to form a powder.

When the dried MCC:CMC powder was redispersed in deionized water, at 2.6% solids, it exhibited at room temperature an initial Brookfield viscosity of 2350 cps and a set-up viscosity after 24 hrs of 7200 cps. When the 2.6% solids dispersion was measured after 24 hrs set-up by a Texas Instrument Rheometer, it exhibited a gel strength G' of 68 Pa. A colloidal content of 90% was obtained, which was determined by centrifugation of the water dispersion at 8250 rpm for 15 minutes followed by gravimetric analysis of the dried supernatant portion.

Example 2

Using 43% Solids Wetcake to Make Colloidal MCC:CMC

Microcrystalline cellulose wetcake was obtained by acid hydrolysis cooking from the FMC facility (Newark, Del., USA). The MCC wetcake solids content was adjusted to 43% with a lab drying oven. In a Hobart mixer, the MCC wetcake was admixed with Aqualon®7LF CMC (Ashland, Inc., Wilmington, Del., USA) in a ratio of 85:15 parts by weight for several minutes. The admixture was passed through a co-rotating twin-screw extruder several times with high extrusion intensity. The MCC:CMC extrudate was then re-dispersed in deionized water. The resulting slurry was passed through a Manton Gaulin homogenizer at 2500 to 3000 psi and spray dried on a 3 foot Bowen spray dryer to form a powder.

When the dried MCC:CMC powder was redispersed in deionized water, at 2.6% solids, it exhibited at room temperature an initial Brookfield viscosity of 1521 cps and a set-up viscosity after 24 hrs of 5900 cps. The 2.6% solids dispersion was measured after 24 hrs set-up by a Texas Instruments Rheometer and exhibited a gel strength G' of 60 Pa. A colloidal content of 93% was obtained.

(Comparative) Example 3

Using 40% Solids Wetcake to Make Colloidal MCC:CMC

Microcrystalline cellulose wetcake was obtained by acid hydrolysis cooking. MCC wetcake solids content was adjusted to 40% with a lab drying oven. In a Hobart mixer, the MCC wetcake was admixed with Aqualon®7LF CMC (Ashland, Inc., Wilmington, Del., USA) in a ratio of 85:15 parts by weight for several minutes. The admixture was passed through a co-rotating twin-screw extruder several times. The MCC:CMC extrudate was then dispersed in deionized water. The resulting slurry was passed through a Manton Gaulin homogenizer at 2500 to 3000 psi and spray dried on a 3 foot Bowen spray dryer to form a powder.

When the dried MCC:CMC powder was re-dispersed in deionized water, at 2.6% solids, it exhibited at room temperature an initial Brookfield viscosity of 720 cps and a set-up viscosity after 24 hrs of 2400 cps. When the 2.6% solids dispersion was measured after 24 hrs set-up by a Texas Instrument Rheometer, it exhibited a gel strength G' of 10-12 Pa. The colloidal content was 77.7%.

Example 4

Dry Colloidal MCC Powder, MCC Wetcake, and CMC Co-Attrited

The following materials were blended: (1) 40 lb of AVICEL®612 dry powder (85% MCC, 15% LVF CMC, bulk dried); (2) 50 lb of 7LVF CMC dry powder (AkzoNobel, Stenungsund, Sweden); and (3) 561 lbs of MCC wetcake at 41% solids (230 lb on dry basis). The MCC wetcake was obtained by acid hydrolysis cooking. The admixture was passed through a co-rotating twin-screw extruder several times with high extrusion intensity. The MCC:CMC extrudate was then bulk dried (fluid bed) and ground to form a powder.

When the dried MCC:CMC product powder (82.5% MCC, 17.5% CMC) was re-dispersed in deionized water at 2.6% solids, the dispersion exhibited at room temperature an initial Brookfield viscosity of 1600 cps and a set-up viscosity after 24 hrs of 6400 cps. The 2.6% solids dispersion was measured after 24 hrs set-up by a Texas Instruments Rheometer and exhibited a gel strength G' of 35 Pa. The colloidal content was 76%.

The use of the dry AVICEL®CL612 powders increased the solids level during extrusion, resulting in a total solids content in the range of 55-66% solids for this specific case. The MCC portion of solids was boosted from 41% solids in the starting wetcake to 44% MCC solids in the resulting MCC:CMC admixture extrudant.

Example 5

Extended MCC Cooking for Increased Extrusion/Attrition Intensity

The MCC wetcake was obtained by acid hydrolysis cooking at 100° C., for 4 hrs, with 2.5% HCl acid concentration. The MCC wetcake with a 40% solids level obtained from this extended acid hydrolysis cooking was co-extruded with 7LF CMC (Ashland) in a weight ratio of 85:15. The extrudate was then dispersed and spray dried to form the product powder.

When the dried MCC:CMC product powder was re-dispersed in deionized water, at 2.6% solids, it exhibited at room temperature an initial Brookfield viscosity of 2500 cps, and a set-up viscosity after 24 hrs of 5500 cps. The 2.6% solids dispersion was measured after 24 hrs set-up by a Texas Instruments Rheometer and exhibited a gel strength G' of 70 Pa. The colloidal content was 88%.

Example 6

Extrusion of 45% Solids MCC Wetcake with a Mix of Low and Medium Viscosity CMCs of Low DS Microcrystalline cellulose wetcake was obtained by acid hydrolysis cooking. The MCC wetcake solids content was adjusted to 45% with a lab drying oven. In a Hobart mixer, the MCC wetcake was admixed with a mix of Aqualon®7LF CMC and 7MF CMC (Ashland, Inc., Wilmington, Del., USA) in a ratio of 88:8:4 parts by weight, respectively, for several minutes. The admixture was passed through a co-rotating twin-screw extruder several times with high extrusion intensity. The MCC:CMC extrudate was then re-dispersed in deionized water. The resulting slurry was spray dried on a 3 foot Bowen spray dryer to form a powder.

When the dried MCC:7LF CMC:7MF CMC powder was redispersed in deionized water, at 2.6% solids, it exhibited at room temperature an initial Brookfield viscosity of 3100 cps and a set-up viscosity after 24 hrs of 5050 cps. The 2.6% solids dispersion was measured after 24 hrs set-up by a Texas Instruments Rheometer and exhibited a gel strength G' of 68 Pa.

Example 7

Extended Extrusion of MCC/CMC Extrudant Comprising Medium Viscosity CMC of Low DS An MCC wet cake was extruded with CMC comprising low DS medium viscosity CMC to generate an extrudant, and the extrudant was then subsequently spray dried to generate a powder composition. The rheological properties were as described in previous sections as in "Comparative Material 3". This product had a gel strength G' at 2.6% solids dispersion in the range of about 30 Pa. This is a comparative sample.

As an experiment within the scope of the invention, the extrudant (before spray drying) above was further extruded by one more pass in a lab co-rotating twin-screw extruder. This further extruded MCC:CMCs extrudate was then re-dispersed in deionized water. The resulting slurry was spray dried on a 3 foot Bowen spray dryer to form a powder. When this powder was redispersed in deionized water, at 2.6% solids, it exhibited at room temperature an initial Brookfield viscosity of 3700 cps and a set-up viscosity after 24 hrs of 7000 cps. The 2.6% solids dispersion was measured after 24 hrs set-up by a Texas Instruments Rheometer and exhibited a gel strength G' of 70 Pa. A colloidal content of 81.7% was obtained.

Example 8

Extended Extrusion of MCC Wetcake with Low Viscosity CMC of Low DS

Microcrystalline cellulose wetcake was obtained by acid hydrolysis cooking and had a wetcake solids content around 43%. The MCC wetcake was admixed with Aqualon®7LF CMC (Ashland, Inc., Wilmington, Del., USA) in a ratio of 85:15 parts by weight and was extruded with high extrusion intensity. The MCC:CMC extrudate was then dispersed in deionized water and spray dried on a 3 foot Bowen spray dryer to form a powder.

When the dried MCC:CMC product powder was re-dispersed in deionized water, at 2.6% solids, it exhibited at room temperature an initial Brookfield viscosity of 1400 cps, and a set-up viscosity after 24 hrs of 5150 cps. The 2.6% solids dispersion was measured after 24 hrs set-up by a Texas Instruments Rheometer and exhibited a gel strength G' of 37 Pa. The colloidal content was about 86%. This was an example of the present invention.

As an additional experiment of the present invention, the above extrudant (before spray drying) was further extruded by one more pass in a lab co-rotating twin-screw extruder. The further extruded MCC:7LF CMC extrudate was then re-dispersed in deionized water. The resulting slurry was spray dried on a 3 foot Bowen spray dryer to form a powder. When this powder was redispersed in deionized water, at 2.6% solids, it exhibited at room temperature an initial Brookfield viscosity of 2400 cps and a set-up viscosity after 24 hrs of 6900 cps. The 2.6% solids dispersion was measured after 24 hrs set-up by a Texas Instruments Rheometer and exhibited a gel strength G' of 60 Pa. A colloidal content of 96.3% was obtained.

Food Applications (FA) Examples

Example FA1

UHT Chocolate Beverages

Materials and Methods:

Samples of a UHT chocolate beverage were prepared using A) a mixture of 0.12% high gel viscosity colloidal MCC based on low DS, low viscosity CMC as described in Examples 1-2 and 120 ppm carrageenan; B) a combination of 0.12% commercially available colloidal MCC based on low DS, low viscosity CMC as described in Material 1 and 120 ppm carrageenan; C) a combination of 0.12% commercially available colloidal MCC based on the high DS CMC described in Material 2 and 120 ppm carrageenan. The formulations are shown in Table FA1.1.

TABLE FA1.1

| Formulation @ 1.5% fat content | Sample A % by wt | Sample B % by wt | Sample C % by wt |
|---|---|---|---|
| Sugar | 7.500 | 7.500 | 7.500 |
| Cocoa Powder D-11 A | 1.500 | 1.500 | 1.500 |
| Carrageenan | 0.012 | 0.012 | 0.012 |
| High Gel Viscosity Colloidal MCC (invention) | 0.120 | — | — |
| Commercial Colloidal MCC Low DS, Low Viscosity CMC | — | 0.200 | — |
| Commercial Colloidal MCC High DS CMC | — | — | 0.120 |
| Pasteurized Semi-Skimmed Milk | to 100 | to 100 | to 100 |

Process:

All powders were dry blended together and mixed for approximately 15 minutes in the cold pasteurized milk using a high shear mixer (e.g., type Silverson or equivalent). The product was first preheated at 75° C. for 45 seconds and then sterilized at 142° C. for 5 seconds in a UHT line (e.g., type APV-SPX or equivalent). The product was then cooled to 70-80° C. and passed through a Rannie homogenizer with a two-stage pressure of 180 bars. Finally, the mixture was cooled at 10° C. and aseptically filled in sterile bottles.

Stability index of the resulting materials was measured using a Turbiscan equipment. The product was scanned with a beam of light at 880 nm near infrared; backscattering or transmission was recorded at small intervals (one scan every 40 μm) along the sample. Changes in backscattering indicated changes in particle size or the concentration of particles.

Sample Preparation Prior to Turbiscan Measurements:

1. Turbiscan glass tubes were prepared as follows: Place a sterile tissue in the tubes and wrap them in aluminum foil. Assemble the 3 different parts of the lids and wrap them in aluminum foil.
2. Sterilize the wrapped tubes and lids in the autoclave at 128° C. for 20 minutes.
3. Turn on the aseptic flow cabinet 30 minutes before transferring the product to the Turbiscan tubes. The samples should first reach room temperature (samples should be tempered for 30 minutes if they are coming from the refrigerator).
4. Prepare labels of tubes and set-up the computer (Turbiscan software) and the AGS station at 30° C.
5. Under the aseptic flow cabinet prepare all materials: sterile Turbiscan tubes, labeled lids, sterile pipettes, and samples.
6. Just before the transfer, clean hands with aseptic solution and gently shake each sample (five times upside down).
7. Open sample bottle and transfer immediately to the Turbiscan tubes using sterile pipettes of 25 ml and close the lids.
8. Immediately, insert the tube in the AGS station and start scanning. Transfer a maximum of three samples at a time before starting scanning.

Visual parameters and scale are described in Table FA1.2. Turbiscan measurements were made once every hour for 5 days at 30° C.

TABLE FA1.2

| Visual Parameters | Explanation | Standard Scale to be used |
|---|---|---|
| On the 250 ml bottle before any manipulation | | |
| Creaming | Fat separation at the top | 0 = absence; 1 = 0.5 mm; 2 = 0.5 to 1 mm; 3 = 1 to 2 mm; 4 >2 mm. |
| Clear Top Separation | Visual Transparent Layer at the Top | 0 = absence; 1 = >0-2 mm; 2 = >2-4 mm; 3 = >4-6 mm; 4 = >6 mm. |
| Marbling | Clear Layers of Whey Inside the Product (waves) | 0 = absence; 1 = very slight marbling; 2 = slight marbling; 3 = strong marbling (not acceptable); 4 = very strong marbling (not acceptable). |
| Sedimentation Layer | Cocoa or Particles Layer at the Bottom of the Liquid | 0 = absence; 1 = 0.5 mm; 2 = 0.5 to 1 mm; 3 = 1 to 2 mm; 4 >2 mm. |
| In a 250 ml glass beaker or cylinder during and after pouring | | |
| Flow Properties | During pouring evaluate level of ripple until gelled pieces are visible. | 0 = absence of ripple; 1 = slight ripple; 2 = ripple; 3 = strong ripple, makes noise while pouring (not acceptable); 4 = gelled pieces (not acceptable). |
| Sedimentation at the bottom | After pouring, proteins or particles (e.g., cocoa, calcium) are visible at the bottom of the bottle. | 0 = absence of sedimentation; 1 = very slight sedimentation; 2 = slight sedimentation; 3 = strong sedimentation (not acceptable); 4 = very strong sedimentation (not acceptable). |

TABLE FA1.2-continued

| Visual Parameters | Explanation | Standard Scale to be used |
|---|---|---|
| Re-dispersibility | Evaluation of the possibility to re-disperse the sedimentation of proteins or particles (e.g., calcium, cocoa, etc.) when the product is poured multiple times. | 0 = absence of sedimentation; 1 = sedimentation disappears after 1 time redispersing (=2 times poured); 2 = sedimentation disappears after 2 times redispersing; 3 = sedimentation disappears after 3 times redispersing; 4 = sedimentation disappears after 4 times redispersing. |

Evaluation of the Samples:

Results of pH, viscosity, and visual observation after one month storage at 4° C., 22° C., and 30° C. are described in Table FA1.3. pH was measured using a calibrated pHmeter (Inolab). Viscosity was measured at room temperature using a Brookfield LV viscometer with spindle #1 at speed 60 rpm for one minute.

TABLE FA1.3

|  | Sample A | | | Sample B | | | Sample C | | |
|---|---|---|---|---|---|---|---|---|---|
| Tests | 4° C. | 22° C. | 30° C. | 4° C. | 22° C. | 30° C. | 4° C. | 22° C. | 30° C. |
| pH | 6.635 | 6.645 | 6.666 | 6.811 | 6.709 | 6.629 | 6.582 | 6.424 | 6.441 |
| Viscosity (cP) | 55.0 | 45.9 | 57.4 | 63 | 45 | 31.5 | 28.8 | 20.1 | 20.5 |
| Visual parameters before any manipulation: | | | | | | | | | |
| Creaming | 0 | 1 | 0 | 0 | 2 | 1 | 0 | 2 | 2 |
| Top Clear separation | 0 | 1 | 0 | 1 | 1 | 2 | 1 | 0 | 0 |
| Marbling | 0 | 2 | 0 | 1 | 1 | 1 | 1 | 0 | 1 |
| Sedimentation layer | 0 | 0 | 0 | 1 | 1 | 1 | 0 | 1 | 1 |
| In a glass beaker or cylinder during and after pouring: | | | | | | | | | |
| Flow properties | 0 | 1 | 0 | 0 | 1 | 1 | 0 | 1 | 1 |
| Sedimentation at the bottom | 0 | 0 | 0 | 1 | 1 | 1 | 0 | 1 | 0 |
| Redispersibility | 0 | 0 | 0 | 1 | 1 | 1 | 0 | 1 | 0 |

Stability Index results after 5 days measurements (one scan every hour) at 30° C. using Turbiscan equipment are described in Table FA1.4.

TABLE FA1.4

| Stability Index | Sample A | Sample B | Sample C |
|---|---|---|---|
| Bottom of the Sample (5 mm) | 0.41 | 1.28 | 1.18 |
| Total Height of the Sample (54 mm) | 0.60 | 1.32 | 0.91 |
| Top of the Sample (5 mm) | 1.73 | 2.53 | 2.71 |

Conclusion:

Visually, Sample A was stable for one month at 4° C., 22° C., and 30° C. with no or trace serum separation, no or trace cocoa sedimentation, and with no or minimal gelation. Low stability indexes (i.e., better stability in particle concentration) of Sample A confirmed the visual observations and suggested a long term stability of six months. Sample A (invention) demonstrated superior performance.

Example FA2

40° Brix and 50° Brix Bake Stable Fruit Filling Based on Concentrate Raspberry

Samples were prepared using A) a dose range of high gel viscosity colloidal MCC made at FMC based on low DS, low viscosity CMC as described in Examples 1-2; and B) a dose range of commercial colloidal MCC (AVICEL®RC591) as described in Material 3.

| 40° Brix Case Formulation | Sample A % by wt | Sample B % by wt |
|---|---|---|
| Glucose syrup 60 DE | 25 | 25 |
| Sugar | 10 | 10 |
| 65° Brix concentrate raspberry | 9 | 9 |
| Modified Starch | 3.5 | 3.5 |
| Tri sodium citrate powder | 0.15 | 0.15 |
| 50% solution of anhydrate citric acid | 0.1 | 0.1 |
| High gel viscosity colloidal MCC (Present Invention) | 0 to 1.5 | — |
| Commercial colloidal MCC (AVICEL ® RC591) | — | 0 to 1.5 |
| Water | to 100 | to 100 |

| 50° Brix Case Formulation | Sample A % by wt | Sample B % by wt |
|---|---|---|
| Glucose syrup 60 DE | 25 | 25 |
| Sugar | 20 | 20 |

-continued

| 50° Brix Case<br>Formulation | Sample A<br>% by wt | Sample B<br>% by wt |
|---|---|---|
| 65° Brix concentrate raspberry | 9 | 9 |
| Modified Starch | 3.5 | 3.5 |
| Tri sodium citrate powder | 0.15 | 0.15 |
| 50% solution of anhydrate citric acid | 0.1 | 0.1 |
| High gel viscosity colloidal MCC (Invention) | 0 to 1.5 | — |
| Commercial colloidal MCC (AVICEL ® RC591) | — | 0 to 1.5 |
| Water | to 100 | to 100 |

Process:

The colloidal MCC, the other dry powders, and the water were weighed out separately. The colloidal MCC was first dispersed in water with a high shear mixing for 10 minutes using a Silverson mixer or equivalent. Then the glucose syrup was preheated at 40° C. and added with the other dry powders in the previous mixture. Then the product was heated to 90° C. in a water bath while gently mixing. The fruit concentrate was then added and mixed until smooth. Finally the citric acid was added and mixed until smooth and the product was hot filled in appropriate containers.

Bake Stability Test:

Bake stability was determined by measuring shape retention. Shape retention is defined as the capacity of a fruit filling preparation to retain its initial shape and volume after being baked for a definite amount of time at a given temperature. The bakery oven was preheated to 200° C. Cups (30 ml) cups were filled with sample product. The fillings from the 30 ml cups were deposited in the middle of concentric circles on a paper sheet on a bakery sheet on the oven plate. The plate was positioned in the middle of the oven. The spread of the material on the 16 axes of the concentric circles was recorded before and after baking. Fillings were baked at 200° C. for 10 minutes. The averages of the material spread were calculated (i.e., Av before and Av after baking) as percentages.

Evaluation of the Samples:

Results of bake stability are described in Table FA2.1 and Table FA2.2.

TABLE FA2.1

|  | Use Levels | | | |
|---|---|---|---|---|
| % Spread in 40° Brix Case | 0% | 0.5% | 1.0% | 1.5% |
| Sample A (invention) | 48.8 | 43.07 | 11.97 | 3.67 |
| Sample B (RC591) | 48.8 | 31.12 | 14.78 | 6.87 |

TABLE FA2.2

|  | Use Levels % | | | |
|---|---|---|---|---|
| % Spread in 50° Brix Case | 0% | 0.5% | 1.2% | 1.5% |
| Sample A (invention) | 48.8 | 25.2 | 18.8 | 17.9 |
| Sample B (RC591) | 48.8 | 31.5 | 31.5 | 22.8 |

Conclusion:

The Sample A of the present invention showed good to excellent bake stability (i.e., low spread in %) at use levels higher than 1%.

Example FA3

High Calcium Reconstituted Milk

Materials and Methods:

Samples were prepared using A) 0.3% of high gel viscosity colloidal MCC based on low DS, low viscosity weight CMC (43% solids) as described in Example 1 as compared to B) 0.3% of commercial colloidal MCC based on high DS CMC as described in Material 2 in a high calcium reconstituted UHT milk. The formulations are set out in Table FA3.1.

TABLE FA3.1

| Formulation/Ingredients | Sample A<br>% by wt | Sample B<br>% by wt |
|---|---|---|
| Milk Powder | 12.00 | 12.00 |
| Calcium Carbonate | 0.23 | 0.23 |
| High Gel Viscosity Colloidal MCC (invention) | 0.30 | — |
| Commercial Colloidal MCC High DS CMC | — | 0.30 |
| Water | to 100 | to 100 |

Process:

The milk powder was added into water at 45° to 50° C. and the product was mixed vigorously for 20 minutes. The reconstituted milk was then heated to 60° to 65° C.

The calcium carbonate and the colloidal MCC were dry blended and added to the milk while mixed vigorously for 5 minutes. The pH was checked and recorded. If required, a buffer of disodium phosphate was added to reach the pH 6.70 to 6.80. The product was then preheated to 70° C. and passed through a homogenizer with a two-stage pressure of 200 bars. The product was heated at 90° C. for 30 seconds and then heated to 140° C. for 10 seconds. Finally the product was cooled at 20° to 25° C. and filled in sterile bottles. Viscosity was measured at room temperature using a Brookfield DV-II+ viscometer at a speed of 30 rpm for 1 minute.

Evaluation of the Samples

Results of viscosity and visual observations after 40 days storage at 22° C. are described in Table FA3.2.

TABLE FA3.2

|  | Sample A | Sample B |
|---|---|---|
| Viscosity (cP) | 7.38 | 11.50 |
| Calcium sedimentation layer | 0 | 0 |

Conclusion:

Visually, Sample A was stable for 40 days at 22° C. with no calcium sedimentation and minimal viscosity.

Example FA4

Retorted Chocolate Milk

Materials and Methods

Samples of retorted chocolate milk were prepared using A) 0.2% of high gel viscosity colloidal MCC based on low DS, low molecular weight CMC as described in Examples 1 and 2 as compared to B) 0.2% of commercial colloidal MCC based on high DS CMC as described in Material 2. The formulations are set out in Table FA4.1.

TABLE FA4.1

| Formulation/Ingredients | Sample A % by wt | Sample B % by wt |
| --- | --- | --- |
| Milk Powder | 2.40 | 2.40 |
| Sugar | 6.50 | 6.50 |
| Cocoa Powder | 1.00 | 1.00 |
| Mono-diglyceride emulsifier | 0.10 | 0.10 |
| High Gel Viscosity Colloidal MCC (invention) | 0.2 | — |
| Commercial Colloidal MCC High DS CMC | — | 0.2 |
| Water | to 100 | to 100 |

Process:

The milk powder was added into water at 45° C. to 50° C. and the product was mixed vigorously for 20 minutes. The reconstituted milk was then heated to 60° to 65° C. The calcium carbonate and the colloidal MCC were dry blended and added to the milk while mixing vigorously for 5 minutes. The pH was checked and recorded. If required, a buffer of disodium phosphate was added to obtain a pH of 6.70 to 6.80. The product was then preheated to 70° C. and passed through a homogenizer with a two-stage pressure of 200 bar. The product was introduced into cans and sealed. Finally, the cans were rotary retorted at 121° C. for 20 minutes. Viscosity was measured at room temperature using a Brookfield DV-II+ viscometer with spindle S00 at speed 30 rpm during 1 minute.

Measurements of the Samples:

Results of viscosity and visual observation after one month storage at 22° C. are described in Table FA4.2.

TABLE FA4.2

|  | Sample A | Sample B |
| --- | --- | --- |
| Viscosity (cP) | 4.11 | 4.31 |
| Cocoa sedimentation layer | 0 | 1 |

Conclusion:

Visually Sample A was stable for one month at 22° C. with no cocoa sedimentation and minimal viscosity.

What is claimed is:

1. A stabilizer composition consisting of:
   a. microcrystalline cellulose; and
   b. water-soluble carboxymethylcellulose having a low viscosity and a degree of substitution of about 0.45 to about 0.85,
   wherein the weight ratio of the microcrystalline cellulose and the carboxymethylcellulose is from about 95:5 to about 70:30, and, upon dispersion in water at 2.6% solids, the stabilizer composition has an initial viscosity of at least 750 cps, a set-up viscosity of at least 2900 cps, and a set-up gel strength G' of at least 20 Pa and wherein said stabilizer composition is produced by the extrusion of an admixture of said microcrystalline cellulose in the form of a wetcake having at least 42% solids with said water-soluble carboxymethylcellulose.

2. The stabilizer composition of claim 1 wherein the carboxymethylcellulose is an alkali metal carboxymethylcellulose.

3. The stabilizer composition of claim 2 wherein the carboxymethylcellulose is sodium carboxymethylcellulose.

4. The composition of claim 3 wherein the carboxymethylcellulose has a degree of substitution of 0.45 to 0.80.

5. The composition of claim 4 wherein the carboxymethylcellulose has a degree of substitution of about 0.7.

6. The composition of claim 1 wherein the initial viscosity is 750 cps to 3000 cps.

7. The composition of claim 1 wherein the set-up viscosity is 3000 cps to 7200 cps.

8. The composition of claim 1 wherein the set-up gel strength G' is 30 Pa to 100 Pa.

9. A stabilizer composition consisting of:
   a) microcrystalline cellulose;
   b) water-soluble carboxymethylcellulose having a medium viscosity and a degree of substitution of 0.45-0.85: and
   c) optionally a water-soluble carboxymethylcellulose having a low viscosity and a degree of substitution of 0.45-0.85;
   wherein the weight ratio of the microcrystalline cellulose and the carboxymethylcellulose component b) is from about 95:5 to about 70:30, and, upon dispersal in water at 2.6% solids, the stabilizer composition has an initial viscosity of at least 1000 cps, a set-up viscosity of at least 3500 cps, and a set-up gel strength G' of at least 40 Pa and wherein said stabilizer composition is produced by the extrusion of an admixture of said microcrystalline cellulose in the form of a wetcake having at least 42% solids with said water-soluble carboxymethylcellulose.

10. The composition of claim 9 wherein component b) is an alkali metal carboxymethylcellulose.

11. The stabilizer composition of claim 10 wherein the alkali carboxymethylcellulose is sodium carboxymethylcellulose.

12. The composition of claim 10 wherein component b) has a degree of substitution of 0.45 to 0.80.

13. The composition of claim 12 wherein component b) has a degree of substitution of about 0.7.

14. The composition of claim 9 wherein the set-up gel strength G' is 45 Pa to 100 Pa.

15. The composition of claim 9 wherein the set-up viscosity is 3500 cps to 7200 cps.

16. The composition of claim 9 wherein the initial viscosity is 1000 cps to 3000 cps.

17. The composition of claim 1 wherein the weight ratio of the microcrystalline cellulose and the carboxymethylcellulose is about 85:15.

18. An edible food product comprising the stabilizer composition of claim 1 or 9.

19. The food product of claim 18 further comprising at least one food selected from the group consisting of fruit, vegetable, grain, nut, meat, and dairy foods.

20. The food product of claim 19 in the form of an emulsion, beverage, sauce, soup, syrup, dressing, film, frozen dessert, cultured food, bakery filling, bakery cream, ultra high temperature and retort processed protein and nutritional beverage, ultra high temperature processed low pH protein-based beverage, ultra high temperature Ca-fortified beverage, high temperature and retort processed milk cream, aerated dairy food system, and aerated non-dairy food system.

21. An industrial suspension comprising the composition of claim 1, wherein the industrial suspension is adapted for use in a pharmaceutical product, a nutraceutical product, a cosmetic product, a personal care product, a consumer product, a agricultural product, or a chemical formulation.

22. The industrial suspension of claim 21 wherein the carboxymethylcellulose is sodium carboxymethylcellulose.

23. A method of making the stabilizer composition of claim 1 comprising the steps of:
   a. mixing a microcrystalline cellulose wetcake having at least 42.0% solids with a water-soluble carboxymethylcellulose having a low viscosity and a degree of substitution of about 0.45 to about 0.85, wherein the weight ratio of the microcrystalline cellulose and the carboxymethylcellulose is from about 95:5 to about 70:30;
   b. extruding the admixture of step a) under high shear and high compression; and
   c. drying the extruded product of step b).

24. The method of claim 23 wherein the drying step c is by spray drying, fluidized bed drying, flash drying, or bulk drying.

25. The method of claim 24 wherein the MCC wetcake solids content is 42.5% to 50%.

26. A method of making a stabilizer composition having improved gel strength G', the method comprising:
   a. mixing
      i. a microcrystalline cellulose wetcake;
      ii. a dry colloidal microcrystalline cellulose; and
      iii. a water-soluble carboxymethylcellulose having a degree of substitution of 0.45 to 0.85,
   wherein the weight ratio of the microcrystalline cellulose and the carboxymethylcellulose after step a) is from about 95:5 to about 70:30 and the total MCC solids content of a.i. and a.ii. is at least 42%;
   b. extruding the admixture of step a); and
   c. drying the extruded product of step b),
   wherein, upon dispersion in deionized water at 2.6% solids, the product of step c) has an initial viscosity of at least 750 cps, a set up viscosity after 24 hours of at least 2900 cps, and a gel strength G' of at least 35 Pa.

27. The method of claim 26 wherein the total MCC solids content of a.i. and a.ii.) is 42.5% to 50%.

28. The method of claim 26 wherein the drying step c is by spray drying, fluidized bed drying, flash drying, or bulk drying.

29. The composition of claim 9 wherein the weight ratio of the microcrystalline cellulose and the carboxymethylcellulose is about 85:15.

30. An edible food product comprising the stabilizer composition of claim 9.

31. A method of making the stabilizer composition of claim 9 comprising the steps of:
   a. mixing a microcrystalline cellulose wetcake having at least 42.0% solids with a water-soluble carboxymethylcellulose having a medium viscosity and a degree of substitution of about 0.45 to about 0.85, wherein the weight ratio of the microcrystalline cellulose and the carboxymethylcellulose is from about 95:5 to about 70:30;
   b. extruding the admixture of step a) under high shear and high compression; and
   c. drying the extruded product of step b).

32. An industrial suspension comprising the composition of claim 9, wherein the industrial suspension is adapted for use in a pharmaceutical product, a nutraceutical product, a cosmetic product, a personal care product, a consumer product, a agricultural product, or a chemical formulation.

33. The composition of claim 9 wherein such composition contains a water-soluble carboxymethylcellulose having a low viscosity and a degree of substitution of 0.45-0.85.

* * * * *